United States Patent
Castellano

(10) Patent No.: US 6,223,786 B1
(45) Date of Patent: May 1, 2001

(54) APPARATUS AND METHOD FOR MIXING MEDICATION AND FILLING AN AMPULE OF A NEEDLE-LESS INJECTOR

(75) Inventor: Thomas P. Castellano, Los Angeles, CA (US)

(73) Assignee: Pen Jet Corporation, Los Angeles, CA (US)

( * ) Notice: Subject to any disclaimer, the term of this patent is extended or adjusted under 35 U.S.C. 154(b) by 0 days.

(21) Appl. No.: 09/192,145

(22) Filed: Nov. 14, 1998

(51) Int. Cl.$^7$ .................................. B65B 1/04; B65B 3/04

(52) U.S. Cl. ............................ 141/2; 141/9; 141/18; 141/27; 141/100; 141/312; 141/319; 141/357; 141/383; 141/384; 604/68; 604/82; 604/416

(58) Field of Search ........................... 141/2, 9, 18, 27, 141/100, 311 R, 312, 319–321, 351, 357, 363, 366, 383, 384, 391; 604/48, 56, 68, 82, 416

(56) References Cited

U.S. PATENT DOCUMENTS

| | | |
|---|---|---|
| 2,642,062 | 6/1953 | May . |
| 3,507,276 | 4/1970 | Burgess . |
| 3,688,765 | 9/1972 | Gasaway . |
| 4,031,892 * | 6/1977 | Hurschman .................. 128/218 M |
| 4,338,980 * | 7/1982 | Schwebel et al. .................. 141/18 |
| 4,676,781 | 6/1987 | Phillips et al. . |
| 4,722,728 | 2/1988 | Dixon . |
| 4,743,229 * | 5/1988 | Chu .................................. 604/82 |
| 4,834,149 * | 5/1989 | Fournier ............................ 141/1 |
| 4,874,367 | 10/1989 | Edwards . |
| 4,941,880 | 7/1990 | Burns . |
| 5,009,634 | 4/1991 | Feldman et al. . |
| 5,009,637 | 4/1991 | Newman et al. . |
| 5,024,656 | 6/1991 | Gasaway et al. . |

(List continued on next page.)

FOREIGN PATENT DOCUMENTS

| | | | |
|---|---|---|---|
| 1258019 | 8/1989 | (CA) | .............................. A61M/5/30 |
| 0295917 | 12/1988 | (EP) | . |
| 2749169 | 12/1997 | (FR) | .............................. A61K/9/08 |
| 96192252 * | 6/1996 | (GB) | . |
| 8908469 | 9/1989 | (WO) | .............................. A61M/5/30 |

(List continued on next page.)

Primary Examiner—Timothy L. Maust
(74) Attorney, Agent, or Firm—Pillsbury Winthrop LLP

(57) ABSTRACT

An apparatus for mixing medication and filling an ampule of a needle-less injector suitable for injecting liquid medication includes a reagent holder and a diluent holder. The regent holder is for containing a reagent, and the diluent holder is for containing a diluent. The diluent holder also includes a diluent plunger rod. The reagent holder is coupled to the diluent holder to provide fluid communication between the reagent holder and the diluent holder. The diluent plunger rod is depressed to load the diluent from the diluent holder into the reagent holder to mix with the reagent to produce the liquid medication for filling the ampule. The reagent holder may further include a reagent plunger rod. After the reagent and the diluent are mixed in the reagent holder to produce the liquid medication, the reagent plunger rod is depressed to load the liquid medication back into the diluent holder for filling the ampule. Preferably, the reagent and the diluent are mixed just prior to injection of the liquid medication due to a short shelf life of the liquid medication. Alternatively, an ampule for mixing medication for an injector suitable for injecting liquid medication includes a housing, a separation film and a piston. The housing has an interior for containing a reagent. The separation film is secured in the interior of the housing to seal and secure the reagent in the housing. The separation film also includes removal means for removing the separation film from the interior of the housing. The piston is for containing a diluent in the interior of the housing between the separation film and the piston. Preferably, the removal means of the separation film is used to remove the separation film and break the seal in the interior of the housing to allow mixing of the reagent and the diluent to produce the liquid medication prior to injecting the liquid medication.

2 Claims, 17 Drawing Sheets

U.S. PATENT DOCUMENTS

| | | |
|---|---|---|
| 5,064,413 | 11/1991 | McKinnon et al. . |
| 5,480,381 | 1/1996 | Weston . |
| 5,593,388 | 1/1997 | Phillips . |
| 5,730,723 | 3/1998 | Castellano et al. . |
| 5,851,198 | 12/1998 | Castellano et al. . |
| 5,957,166 * | 9/1999 | Safabash ................................ 141/26 |

FOREIGN PATENT DOCUMENTS

| | | | |
|---|---|---|---|
| WO 9503844 | 2/1995 | (WO) . | |
| 9619252 | 6/1996 | (WO) | ............................. A61M/5/30 |
| WO 9628202 | 9/1996 | (WO) . | |
| 9725015 | 7/1997 | (WO) | ............................... A61J/1/00 |

* cited by examiner

APPARATUS AND METHOD FOR MIXING MEDICATION AND FILLING AN AMPULE OF A NEEDLE-LESS INJECTOR

FIELD OF THE INVENTION

This invention relates to devices and methods for mixing medication and filling an ampule of a needle-less injector prior to an injection, and in particular, embodiments for filling an ampule of a needle-less injector or syringe, with a medication that must be mixed just prior to administration in an injection.

BACKGROUND OF THE INVENTION

Typically, injections are performed with syringes that pierce the skin with a needle to deliver medication to a desired location on a body. In a large number of cases the syringes are pre-filled with a medication. However, if the medication does not have a long shelf life, it must be mixed just prior to an injection to maintain potency. This requires the medication to be mixed externally to the syringe and then drawn in using needles or the like. After drawing in the medication, the injection is administered in a normal manner. But, after the injection there are one or more needles that need to be disposed of, increasing costs and increasing the potential health hazards from exposure to used needles.

As an alternative to needle delivery injections, needle-less medication injections have been performed with "permanent gun" instruments, generally referred to as "jet injectors". These devices use either a compression spring or a compressed inert gas to propel the fluid medication (via a push rod plunger) through a small orifice (an injector nozzle) which rests perpendicular to and against the injection site. The fluid medication is generally accelerated at a high rate to a speed of between about 800 feet per second (fps) and 1,200 fps (approximately 244 and 366 meters per second, respectively). This causes the fluid to pierce through the skin surface without the use of a needle, resulting in the medication being deposited in a flower pattern under the skin surface. These reusable jet injectors can accept pre-loaded medication cartridges, but again the cartridges must be pre-loaded just prior to an injection for certain medications with short shelf lives. The procedure is to again use a needle and a syringe to mix and then load the medication in the cartridge prior to an injection. After drawing in the medication, the needle-less injection is administered in a normal manner. But, after the injection there are again one or more needles that need to be disposed of, increasing costs and increasing the potential health hazards from exposure to used needles.

Single use needle-less jet injectors offer an alternative to multi-use, needle-less injectors, since they are low cost and can be pre-loaded at the point of manufacture. However, if the medication does not have a long shelf life, the pre-loading is impractical. Thus, single-use, needle-less injectors have not been usable with medications that must be mixed prior to injection. An alternative to overcome this drawback was to include a two compartment ampule in the injector, which is opened up with a piercing mechanism and combined together to mix the medication as the injection takes place. Although, this obviates the need for needles, the results are unsatisfactory, since the medication is not always thoroughly mixed and properly deposited under the skin. In addition, improper mixing can allow the medication (particularly large molecule medications) to be destroyed or altered during the injection process. Further, it is possible for the piercing mechanism included in the ampule to break the barrier between diluent and reagent may block or obscure the orifice, or jam the needle-less injector leading to an improper injection.

SUMMARY OF THE DISCLOSURE

It is an object of an embodiment of the present invention to provide an improved device and method for filling an ampule of a needle-less injector, syringe or the like, that obviates for practical purposes, the above-mentioned limitations.

According to an embodiment of the present invention, an apparatus for mixing medication and filling an ampule of a needle-less injector suitable for injecting liquid medication includes a reagent holder and a diluent holder. The regent holder is for containing a reagent, and the diluent holder is for containing a diluent. The diluent holder also includes a diluent plunger rod. In preferred embodiments, the reagent holder is coupled to the diluent holder to provide fluid communication between the reagent holder and the diluent holder. Also, the diluent plunger rod is depressed to load the diluent from the diluent holder into the reagent holder to mix with the reagent to produce the liquid medication for filling the ampule of the needle-less injector. In further embodiments, the reagent holder further includes a reagent plunger rod. After the reagent and the diluent are mixed in the reagent holder to produce the liquid medication, the reagent plunger rod is depressed to load the liquid medication back into the diluent holder for filling the ampule of the needle-less injector. Preferably, the reagent and the diluent are mixed just prior to injection of the liquid medication due to a short shelf life of the liquid medication. Also, the ampule of the needle-less injector is attached to the needle-less injector after filling with the liquid medication.

In particular embodiments, the reagent holder is the ampule of the needle-less injector. In other embodiments, the diluent holder is the ampule of the needle-less injector.

In preferred embodiments of the present invention, a reagent holder for mixing medication and filling an ampule of a needle-less injector suitable for injecting liquid medication includes a housing, and a reagent plunger rod. The housing is for containing a reagent, and includes attachment means (such as snaps or threads) for coupling the housing to the ampule of the needle-less injector containing a diluent. The reagent plunger rod is coupled to the housing to contain the reagent in the housing. When the reagent holder is coupled to the ampule of the needle-less injector by the attachment means, fluid communication is provided between the reagent holder and the ampule of the needle-less injector. In addition, when the diluent plunger rod is depressed to load the diluent into the reagent holder, which moves the reagent plunger rod to accommodate the diluent, the diluent is mixed with the reagent to produce the liquid medication for filing the ampule of the needle-less injector. In further embodiments, after the reagent and the diluent are mixed in the reagent holder to produce the liquid medication, the reagent plunger rod is depressed to load the liquid medication into the ampule of the needle-less injector to fill the ampule of the needle-less injector.

According to further embodiments of the present invention, a method of mixing medication and filling an ampule of a needle-less injector suitable for injecting liquid medication includes the steps of: providing a reagent holder containing a reagent; providing a diluent holder containing a diluent; providing the diluent holder with a diluent plunger rod; coupling the reagent holder to the diluent holder to provide fluid communication between the reagent holder and the diluent holder; and depressing the diluent plunger rod to load the diluent into the reagent holder to mix with the reagent to produce the liquid medication for filling the ampule of the needle-less injector. Further embodiments include the steps of: providing the reagent holder with a reagent plunger rod; and depressing the reagent plunger rod, after the reagent and the diluent are mixed in the reagent holder to produce the liquid medication, to load the liquid medication into the diluent holder for filling the ampule of the needle-less injector. Preferably, the step of mixing the reagent and the diluent occurs just prior to injection of the liquid medication due to a short shelf life of the liquid medication. Also, the method includes the step of attaching the ampule of the needle-less injector to the needle-less injector after filing with the liquid medication.

In particular embodiments, the reagent holder is formed as the ampule of the needle-less injector. In other embodiments, the diluent holder is formed as the ampule of the needle-less injector.

Other features and advantages of the invention will become apparent from the following detailed description, taken in conjunction with the accompanying drawings which illustrate, by way of example, various features of embodiments of the invention.

BRIEF DESCRIPTION OF THE DRAWINGS

A detailed description of embodiments of the invention will be made with reference to the accompanying drawings, wherein like numerals designate corresponding parts in the several figures.

DETAILED DESCRIPTION OF THE PREFERRED EMBODIMENTS

Figure 1:
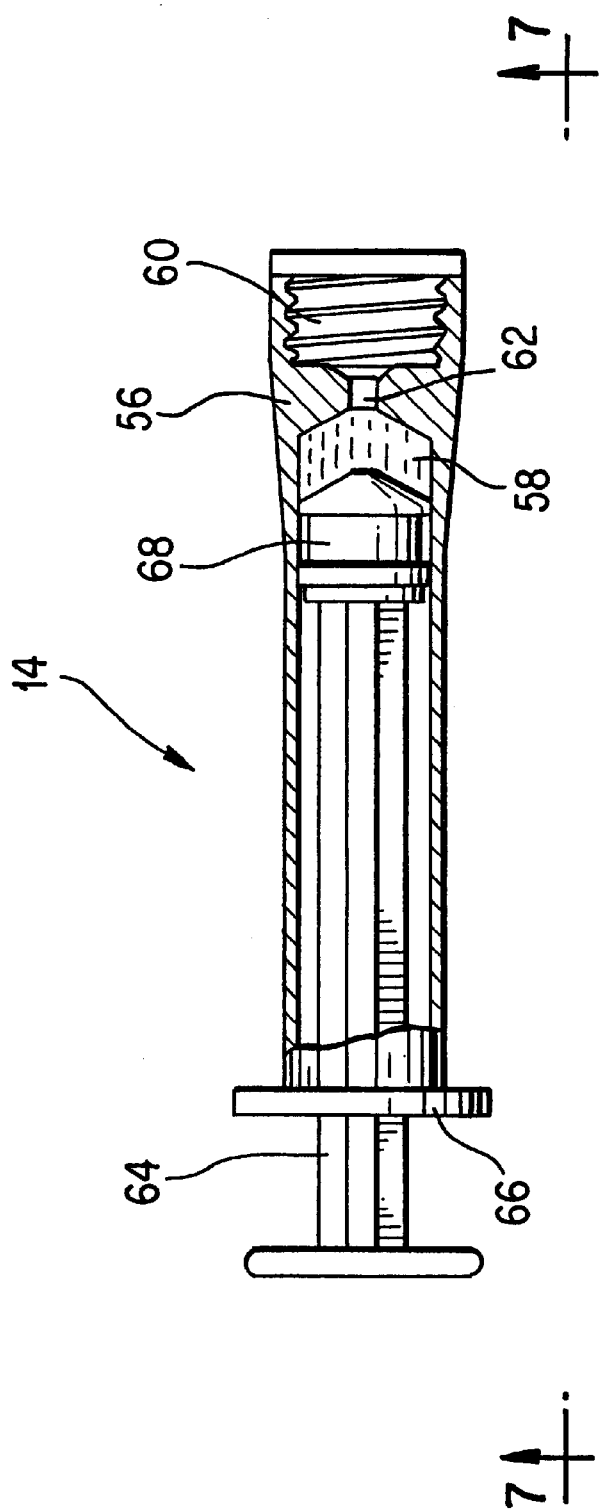
FIG. 1 is a side plan view of a transparent reagent holder in accordance with an embodiment of the present invention.
Figure 3:
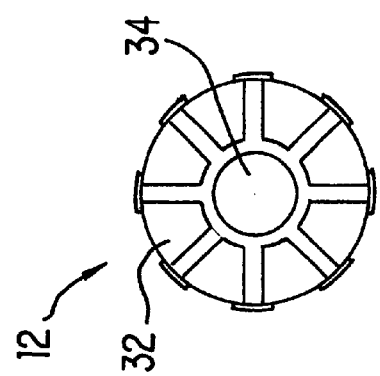
FIG. 3 is an end plan view of the ampule shown in FIG. 2.
Figure 2:
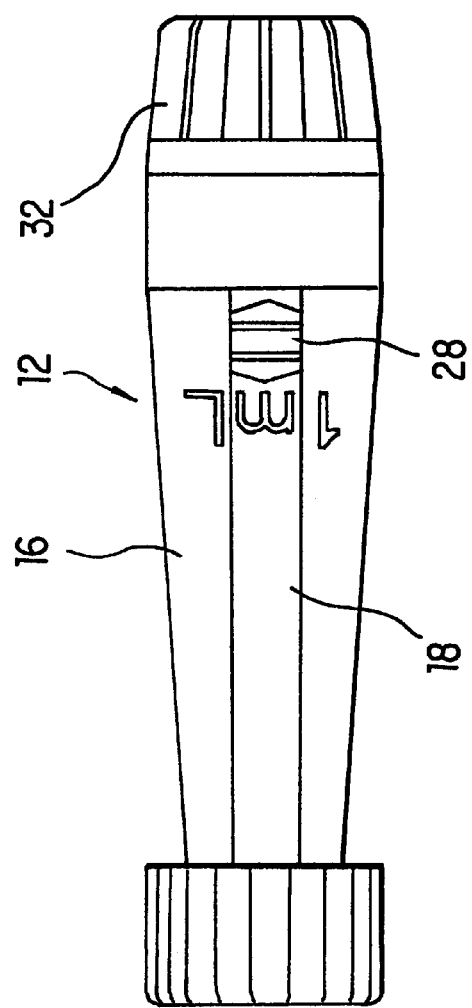
FIG. 2 is a side plan view of an ampule for a needle-less injector in accordance with an embodiment of the present invention.
Figure 4A:
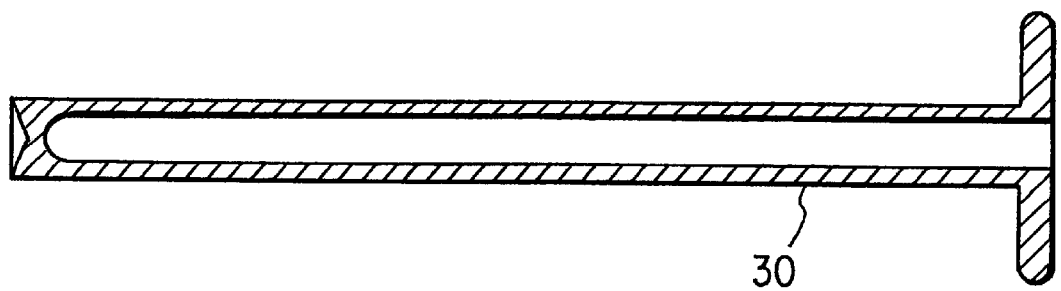
FIG. 4A is a cross-sectional view of a diluent plunger rod in accordance with an embodiment of the present invention.
Figure 4B:
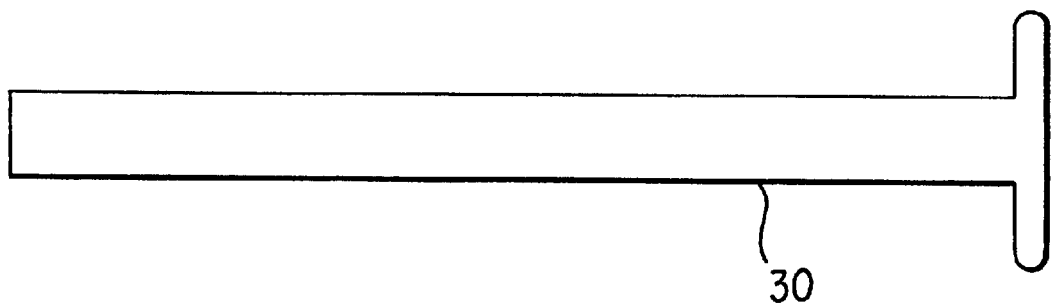
FIG. 4B is a side plan view of a diluent plunger rod in accordance with an embodiment of the present invention.

As shown in the drawings for purposes of illustration, the invention is embodied in a device and method for mixing medication and filling an ampule of a single-use needle-less injector with medication prior to administration of an injection. Preferably, the device is used in conjunction with, or are attached to, a single-use disposable needle-less injector, such as that disclosed in U.S. patent application Ser. No. 5,730,723 filed Sep. 25, 1996 and U.S. Pat. No. 5,851,198 filed Oct. 9, 1996, which are herein incorporated by reference. However, it will be recognized that further embodiments of the invention may be used to mix medication and fill an ampule in multiple-use needle-less injectors, conventional syringes, infusion injections and the like.

FIGS. 1–11 illustrate a filling apparatus 10 in accordance with an embodiment of the present invention. The filling apparatus 10 includes a diluent holder 12 and a reagent holder 14.

The diluent holder 12 is sized to contain a diluent for producing a medication prior to injection. In preferred embodiments, the diluent holder 12 is an ampule for use on a needle-less injector 1000 (see FIG. 11). However, in alternative embodiments, the diluent holder 12 may be another receptacle for loading diluent into another container, such as an ampule for a multiple-use needle-less injector, syringe or the like. The diluent holder 12 includes a housing 16 that forms an interior chamber 18 for holding the diluent. In preferred embodiments, the diluent is sterile water, saline, buffered solution or other solvent that is mixed with a reagent to form a liquid medication. One end of the housing 16 includes threads 20 and an orifice 22 for mating with corresponding threads and opening on the reagent holder 14 to provide fluid communication between the diluent holder 12 and the reagent holder 14. Another end of the housing 16 includes threads 24 and an opening 26 for mating with corresponding needle-less injector 1000. In alternative embodiments, the ends of the diluent holder 12 may be formed with other attachment structures, such as snaps, bars, friction fits or the like.

Figure 5:
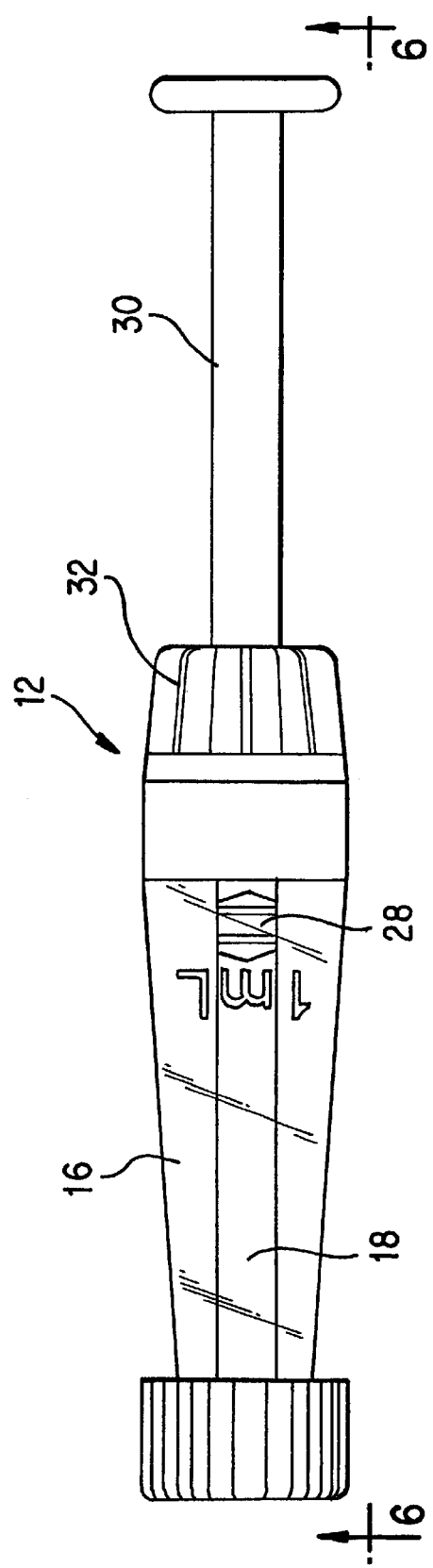
FIG. 5 is a side plan view of the ampule of FIGS. 2 and 3 combined with the plunger rod shown in FIG. 4.
Figure 6:
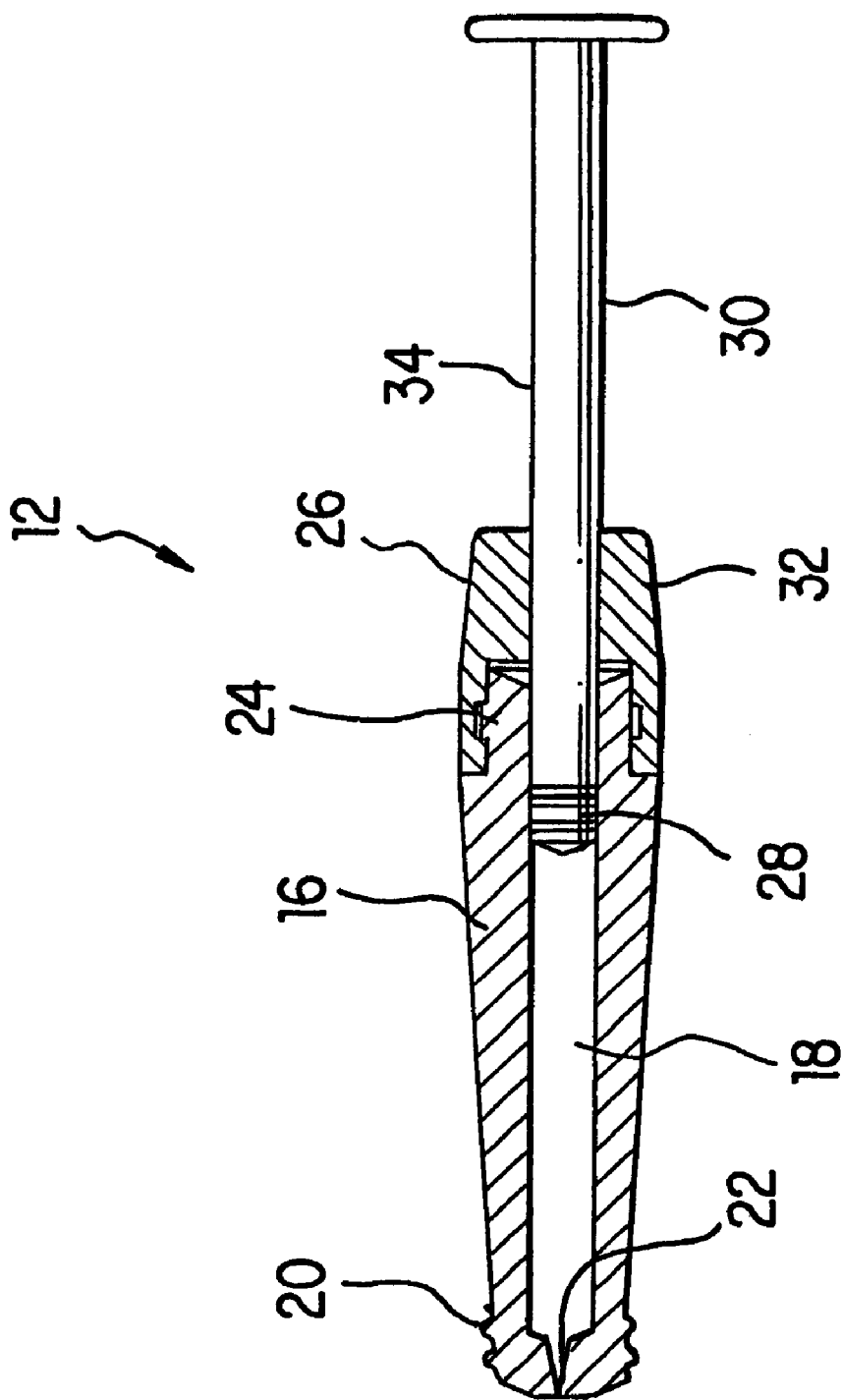
FIG. 6 is a cross-sectional view of the ampule and plunger rod as shown along the line 6—6 in FIG. 5.
Figure 7:
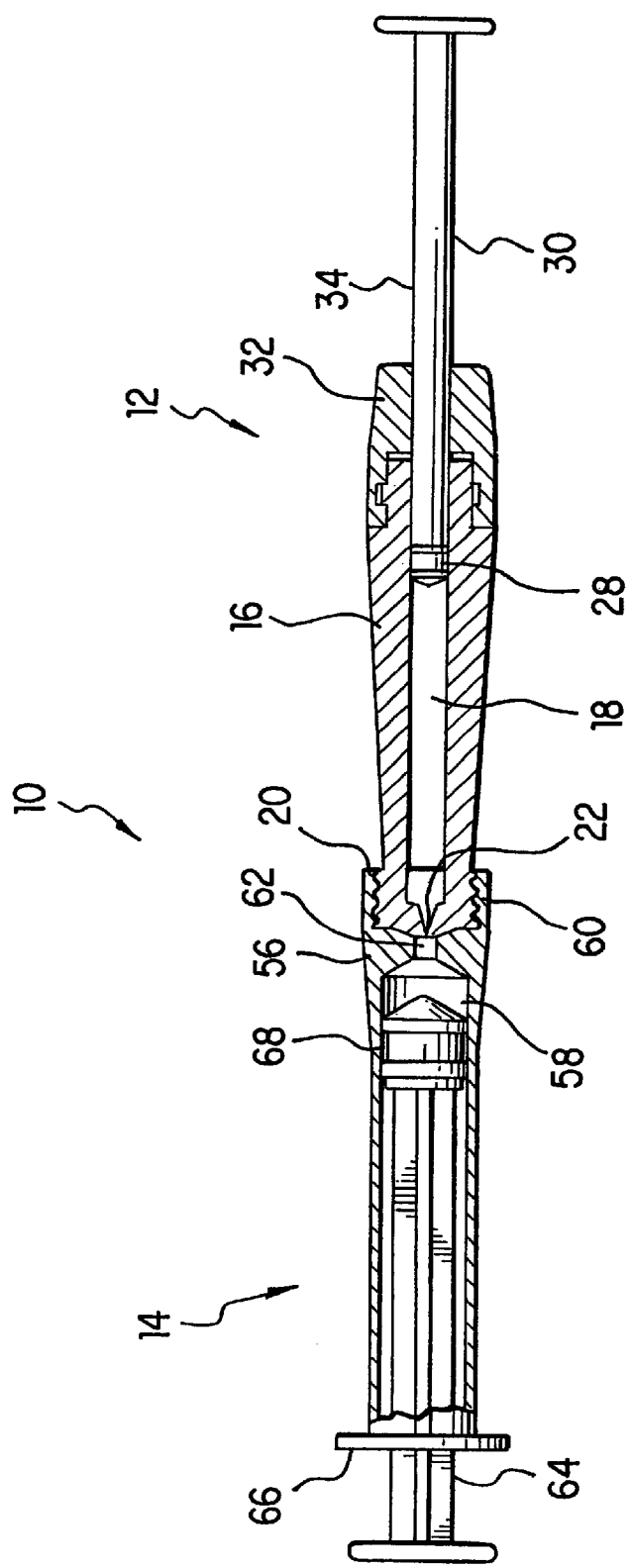
FIG. 7 is a cross-sectional view of the reagent holder, as shown along line 7—7 in FIG. 1 coupled to the ampule and plunger rod as shown in FIG. 6, prior to mixing the reagent and the diluent in the reagent holder.
Figure 8:
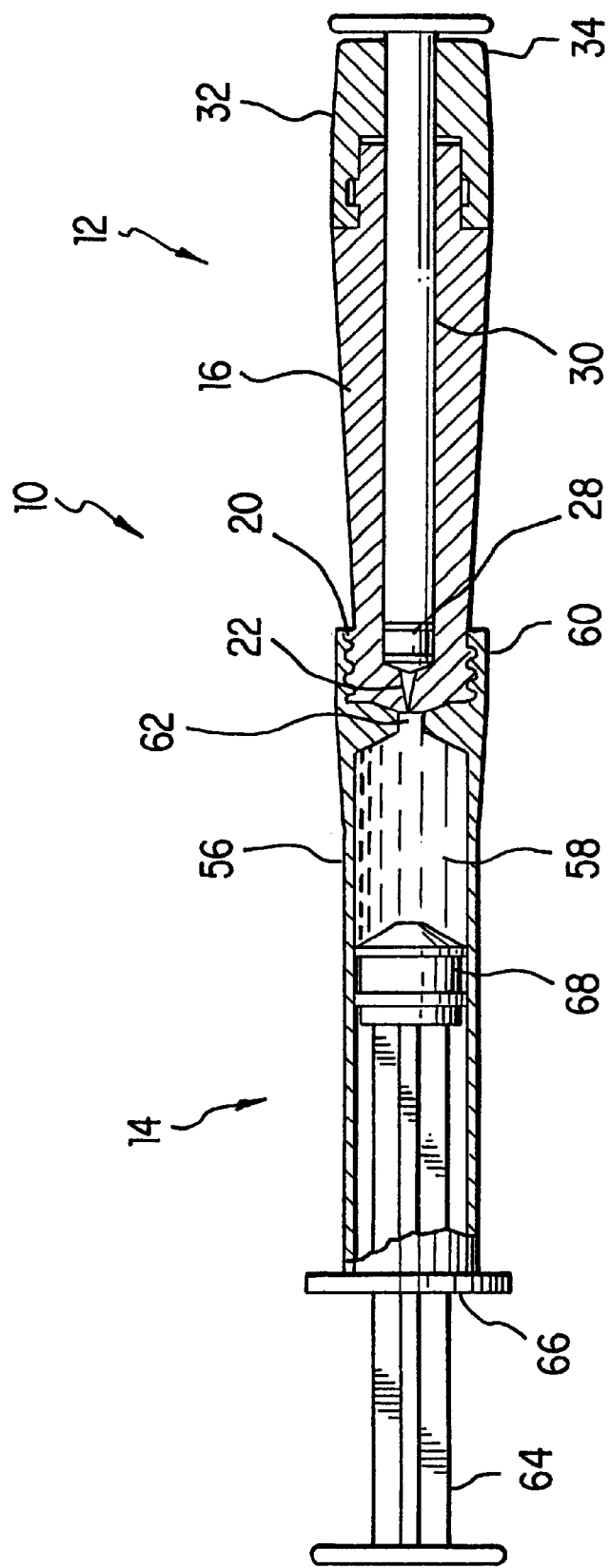
FIG. 8 is a cross-sectional view of the reagent holder and ampule, shown in FIG. 7, after the diluent plunger rod has been depressed to load the diluent into the reagent for mixing.
Figure 9:
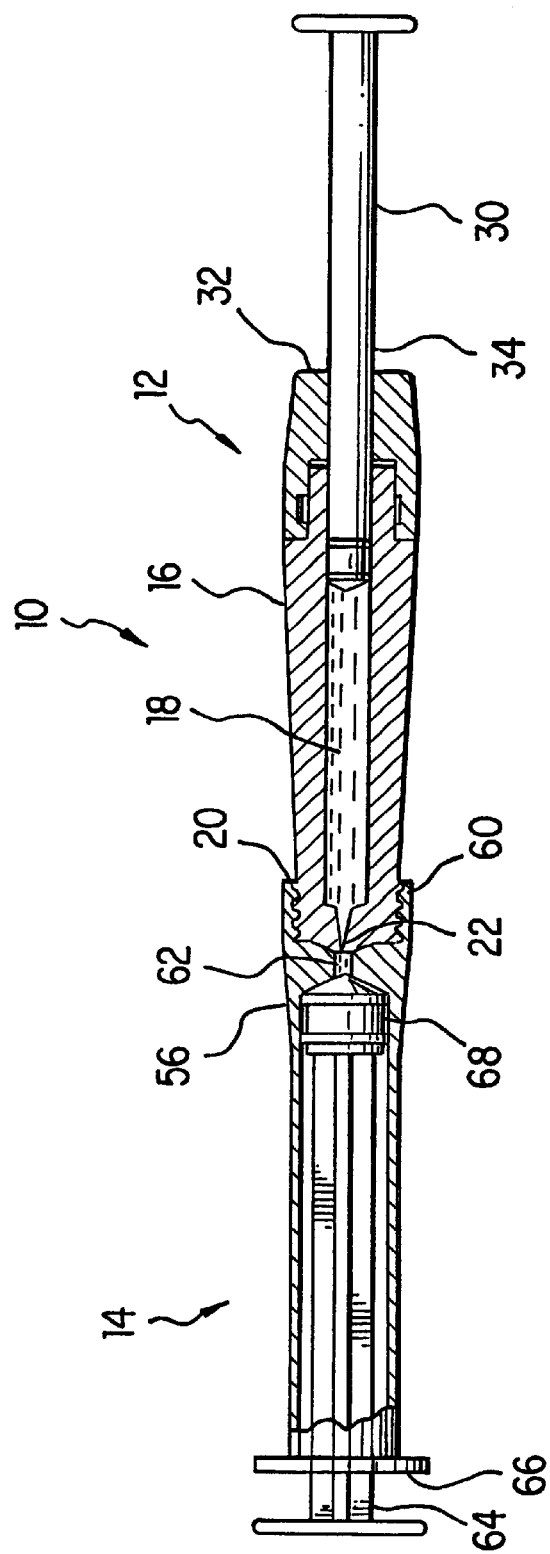
FIG. 9 is a cross-sectional view of the reagent holder and ampule, shown in FIG. 8, after the medication has been mixed and the reagent plunger rod is depressed to reload the mixed reagent and diluent in the ampule for an injection.
Figure 10:
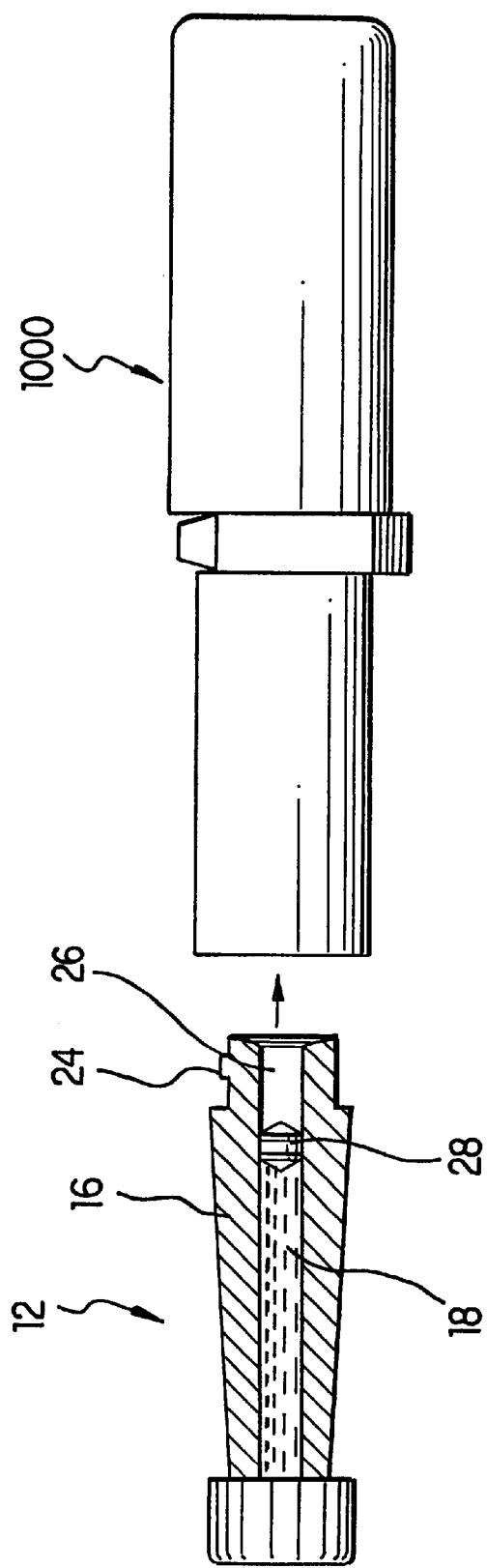
FIG. 10 is a partial cross-sectional view and side plan view of an ampule that is to be mated to a needle-less injector in accordance with an embodiment of the present invention.
Figure 11:
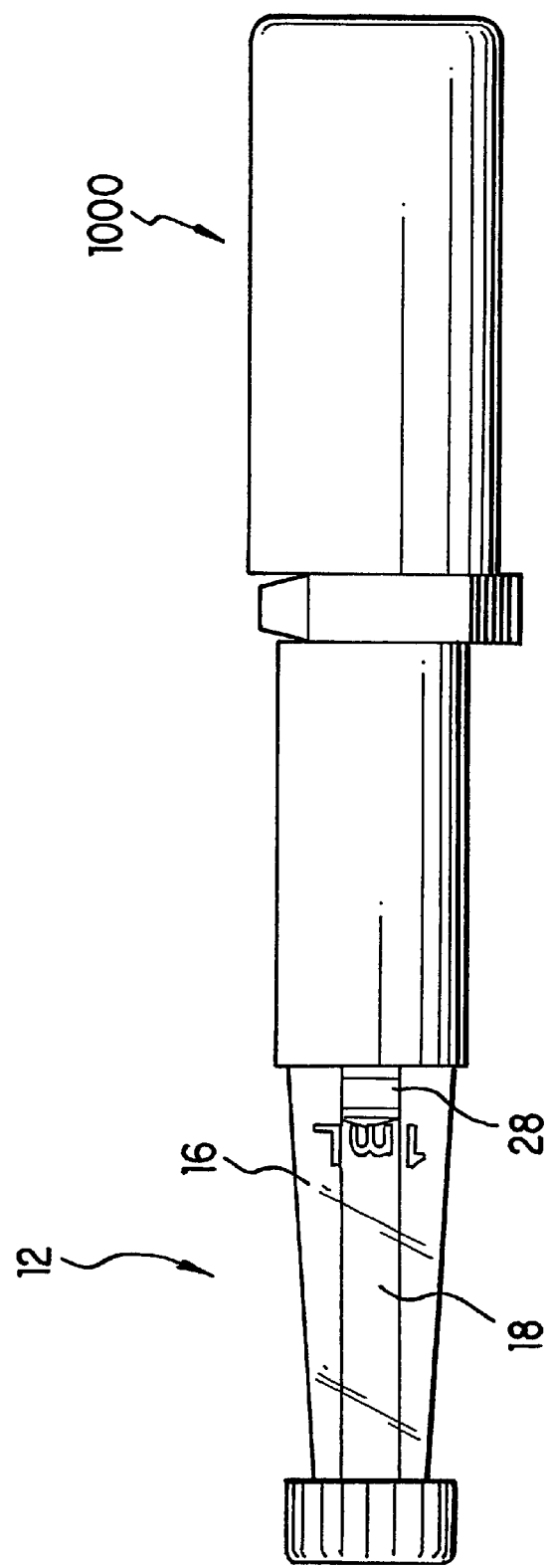
FIG. 11 is a side plan view of the assembled needle-less injector prior to administering an injection in accordance with an embodiment of the present invention.
Figure 12:
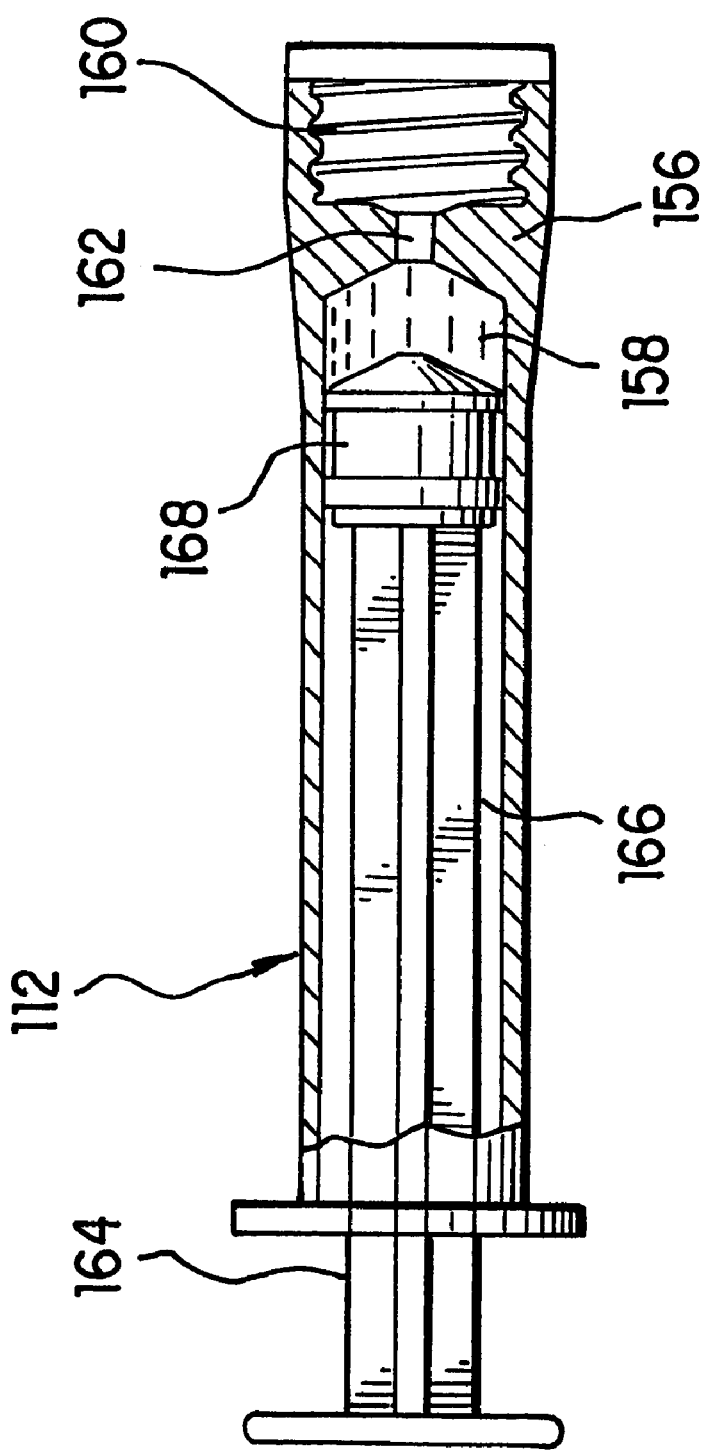
FIG. 12 is a side plan view of a transparent diluent holder in accordance with another embodiment of the present invention.
Figure 13:
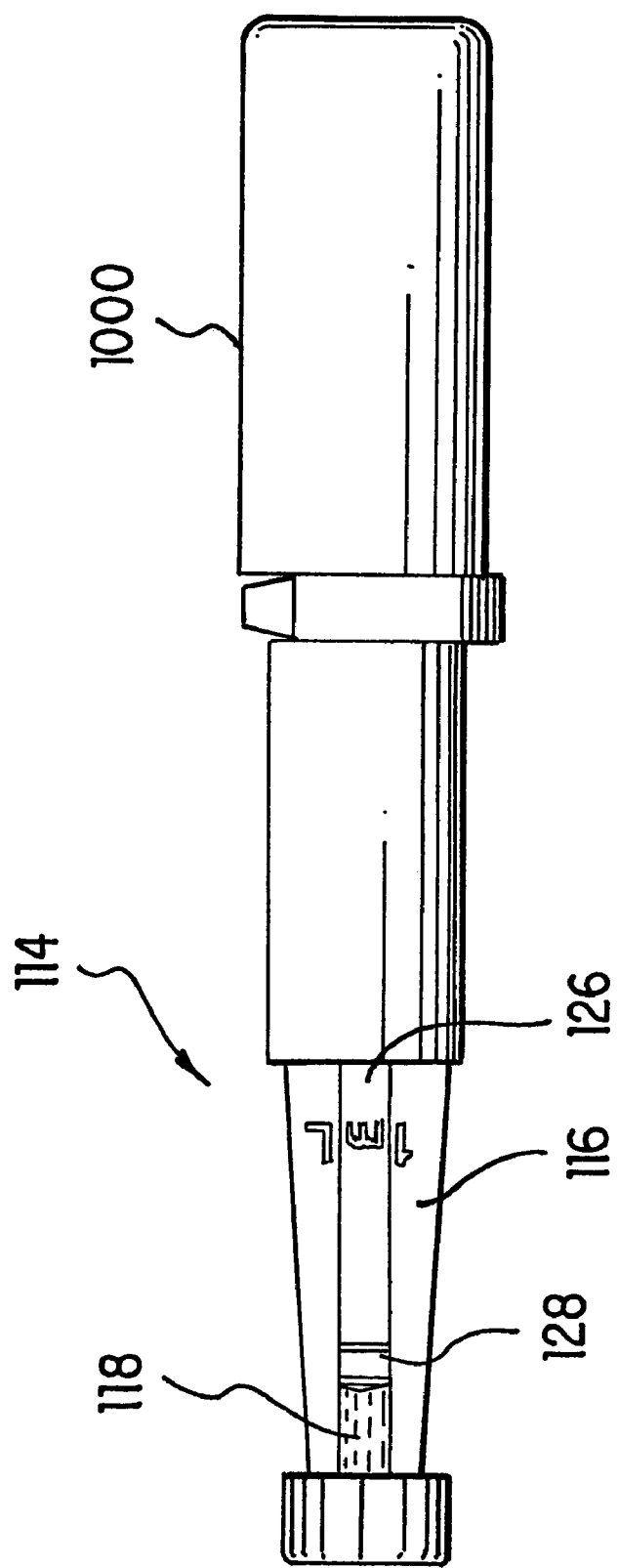
FIG. 13 is a side plan view of an ampule and a needle-less injector in accordance with another embodiment of the present invention.
Figure 14:
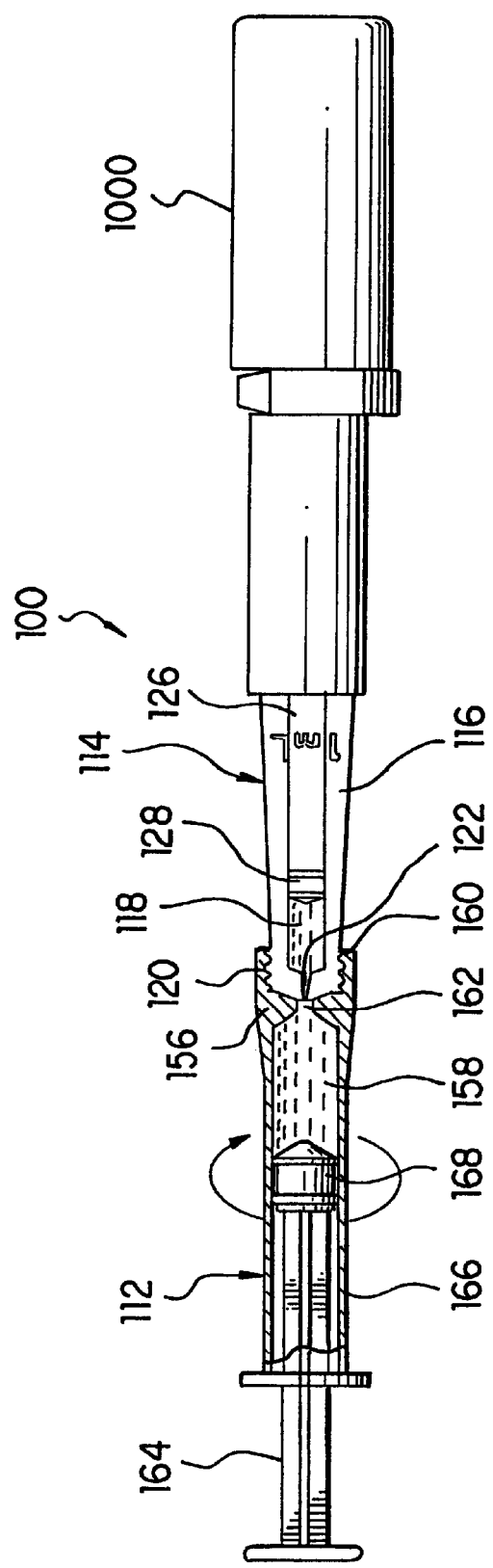
FIG. 14 is a cross-sectional view of the diluent holder coupled to the ampule reagent holder and the needle-less injector prior to mixing the reagent and the diluent in the reagent holder.
Figure 15:
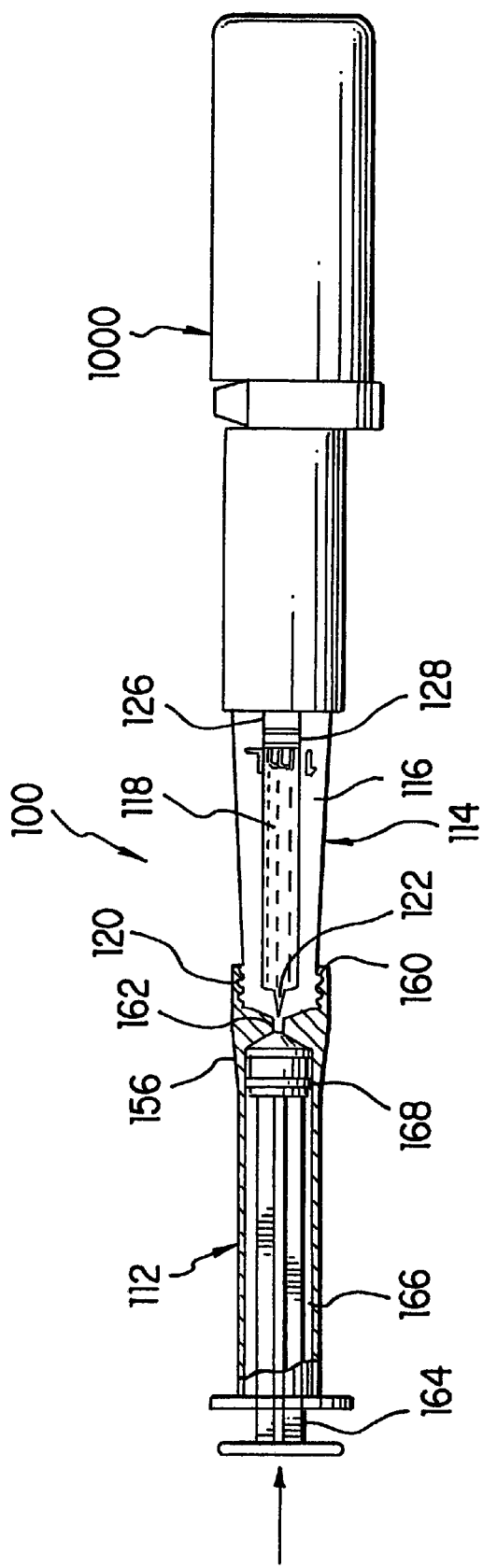
FIG. 15 is a cross-sectional view of the diluent holder coupled to the ampule reagent holder and the needle-less injector after the diluent plunger rod has been depressed to load the diluent into the reagent for mixing.

The diluent holder 12 also includes a piston 28 for maintaining the diluent in the interior chamber 18 and substantially prevent leakage out of the opening 26 of the housing 16. The piston 28 maintains the diluent in the interior chamber 18 so that it does not leak out of the orifice 22. As shown in FIGS. 5–6, the diluent holder includes a diluent plunger 30 and a support bushing 32 having an opening 34 that allows passage of the diluent plunger rod 30 through the support bushing 32 to expel diluent.

The reagent holder 14 is sized to contain a reagent for producing a medication prior to injection when mixed with the diluent of the diluent holder 12. The reagent holder 14 includes a housing 56 that forms an interior chamber 58 for holding the reagent. In preferred embodiments, the reagent or other reagent is needed to produce a liquid medication. One end of the housing 56 includes threads 60 and an opening 62 for mating with corresponding threads 20 and orifice 22 on the diluent holder 12 to provide fluid communication between the diluent holder 12 and the reagent holder 14. In alternative embodiments, the end of the reagent holder 14 may be formed with other attachment structures, such as snaps, bars, friction fits or the like. Another end of the housing 56 includes a reagent plunger 64 and an opening 66 for receiving the reagent plunger 64.

The reagent holder 14 also includes a piston 68 coupled to the end of the reagent plunger 64 for maintaining the reagent in the interior chamber 58 and to substantially prevent leakage out of the opening 66 of the housing 56. The piston 68 maintains the reagent in the interior chamber 58 so that it does not leak out of the opening 62.

As shown in FIGS. 1–11, the reagent holder 14 stores the reagent and is configured for sterile docking (or coupling) with the diluent holder 12 containing the diluent. When the diluent holder 12 is docked with the reagent holder 14, the diluent plunger 30 is pushed through the bushing 32 on the diluent holder 12 to transfer and load the diluent into the reagent holder 14, by moving the diluent plunger 30 and piston 28 towards the orifice 22. As the diluent enters the reagent holder 14, the diluent and reagent are mixed together to produce the medication. Once the medication is produced, the reagent plunger 64 and piston 68 are moved towards the opening 62 in the housing 56 of the reagent holder 14 to reload the mixed medication back into the diluent holder 12. In preferred embodiments, diluent holder 12 is the ampule for a needle-less injector or the like. After reloading the diluent holder 12, the diluent plunger 30 and the bushing 32 are removed and discarded from the diluent holder 12. The diluent holder, if an ampule, is then threaded onto the body of a needle-less injector 1000. Once seated, the reagent holder 14 is removed from the end of diluent holder 12, and final tightening is performed on the diluent holder 12. A needle-less injection is then performed in a normal manner.

In alternative embodiments, if the diluent holder 12 is not an ampule for a needle-less injector, the reagent holder 14, may be removed after receiving the diluent, and then coupled to an ampule for filling with the mixed medication. In further embodiments, the diluent holder 12 may be an ampule for a multi-use needle-less injector, syringe or the like.

FIGS. 12–18 illustrate a filling apparatus 100 in accordance with an embodiment of the present invention. The filling apparatus 100 includes a diluent holder 112 and a reagent holder 114. The filling apparatus 100 is similar to the apparatus 10 described above; however, the filling apparatus 100 contains the reagent in the ampule for a needle-less injector, syringe or the like. This removes one step of reloading the ampule after mixing the reagent and diluent to produce the medication.

The reagent holder 114 is sized to contain a reagent for producing a medication prior to injection. In preferred embodiments, the reagent holder 114 is an ampule for use on a needle-less injector 1000 (see FIG. 11). The reagent holder 114 includes a housing 116 that forms an interior chamber 118 for holding the reagent. In preferred embodiments, the reagent is mixed with a diluent to form a liquid medication. One end of the housing 116 includes threads 120 and an orifice 122 for mating with corresponding threads and opening on the diluent holder 112 to provide fluid communication between the diluent holder 112 and the reagent holder 114. Another end of the housing 116 includes threads (not shown) and an opening 126 for mating with corresponding needle-less injector 1000. In alternative embodiments, the ends of the reagent holder 114 may be formed with other attachment structures, such as snaps, bars, friction fits or the like.

The reagent holder 114 also includes a piston 128 for maintaining the reagent in the interior chamber 118 and substantially prevent leakage out of the opening 126 of the housing 116. The piston 128 maintains the reagent in the interior chamber 118 so that it does not leak out of the orifice 122. As shown in FIGS. 13–18, the reagent holder 114 is attached to the needle-less injector 1000. In alternative embodiments, the reagent holder 14 is filled separately from the needle-less injector 1000 and includes a reagent plunger and a support bushing having an opening that allows passage of the reagent plunger rod through the support bushing to adjust the piston 128 after receipt of the diluent, in a manner and structure similar to that described in the first embodiment above.

The diluent holder 112 is sized to contain a diluent for producing a medication prior to injection when mixed with the reagent of the reagent holder 114. The diluent holder 112 includes a housing 156 that forms an interior chamber 158 for holding the diluent. In preferred embodiments, the diluent is sterile water, saline, buffered solution or other solvent that is mixed with a reagent to form a liquid medication. One end of the housing 156 includes threads 160 and an opening 162 for mating with corresponding threads 120 and orifice 122 on the reagent holder 114 to provide fluid communication between the diluent holder 112 and the reagent holder 114. In alternative embodiments, the end of the diluent holder 112 may be formed with other attachment structures, such as snaps, bars, friction fits or the like. Another end of the housing 156 includes a diluent plunger 164 and an opening 166 for receiving the diluent plunger 164.

The diluent holder 112 also includes a piston 168 coupled to the end of the diluent plunger 164 for maintaining the diluent in the interior chamber 158 and to substantially prevent leakage out of the opening 166 of the housing 156. The piston 168 maintains the diluent in the interior chamber 158 so that it does not leak out of the opening 162.

Figure 16:
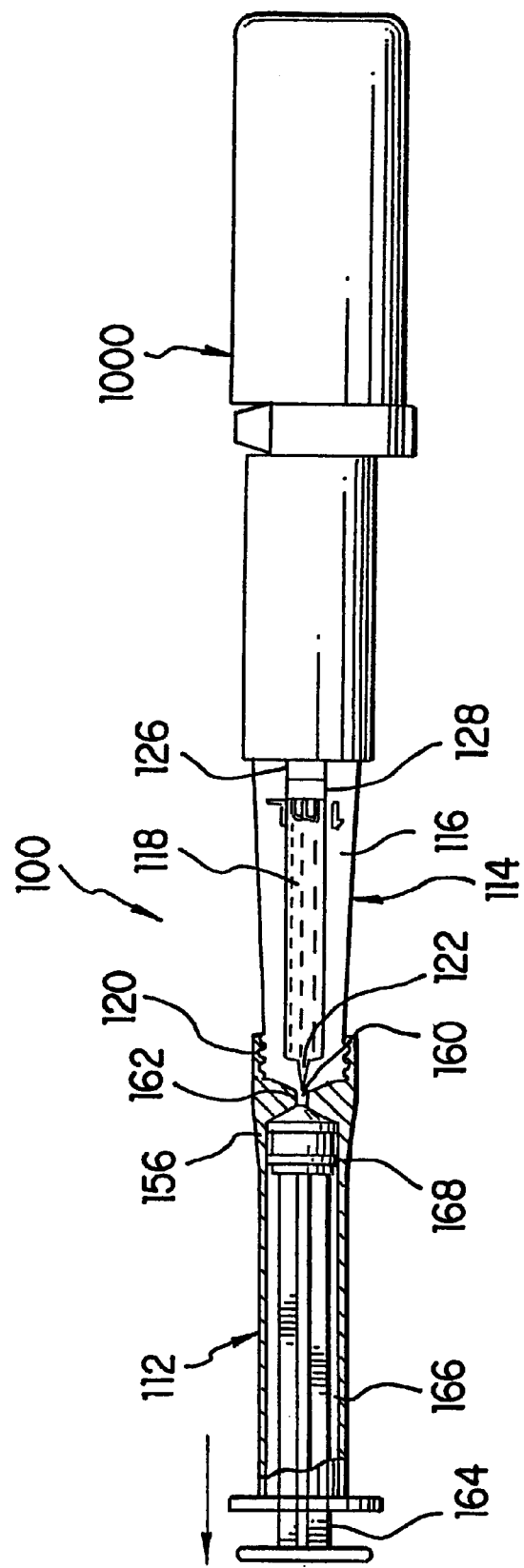
FIG. 16 is a cross-sectional view of the diluent holder coupled to the ampule reagent holder and the needle-less injector after the medication has been mixed and the diluent plunger rod is withdrawn to remove air from the mixed reagent and diluent in the ampule reagent holder.
Figure 17:
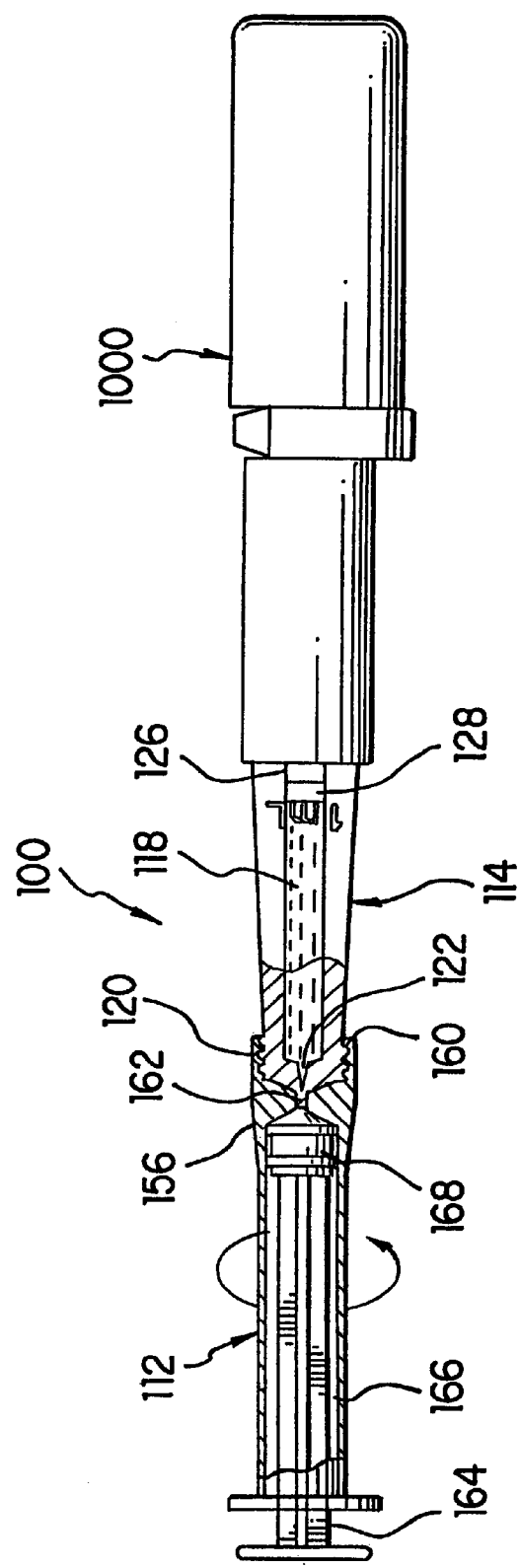
FIG. 17 is a cross-sectional view of a diluent holder coupled to the ampule reagent holder and needle-less injector prior to removal to permit an injection.
Figure 18:
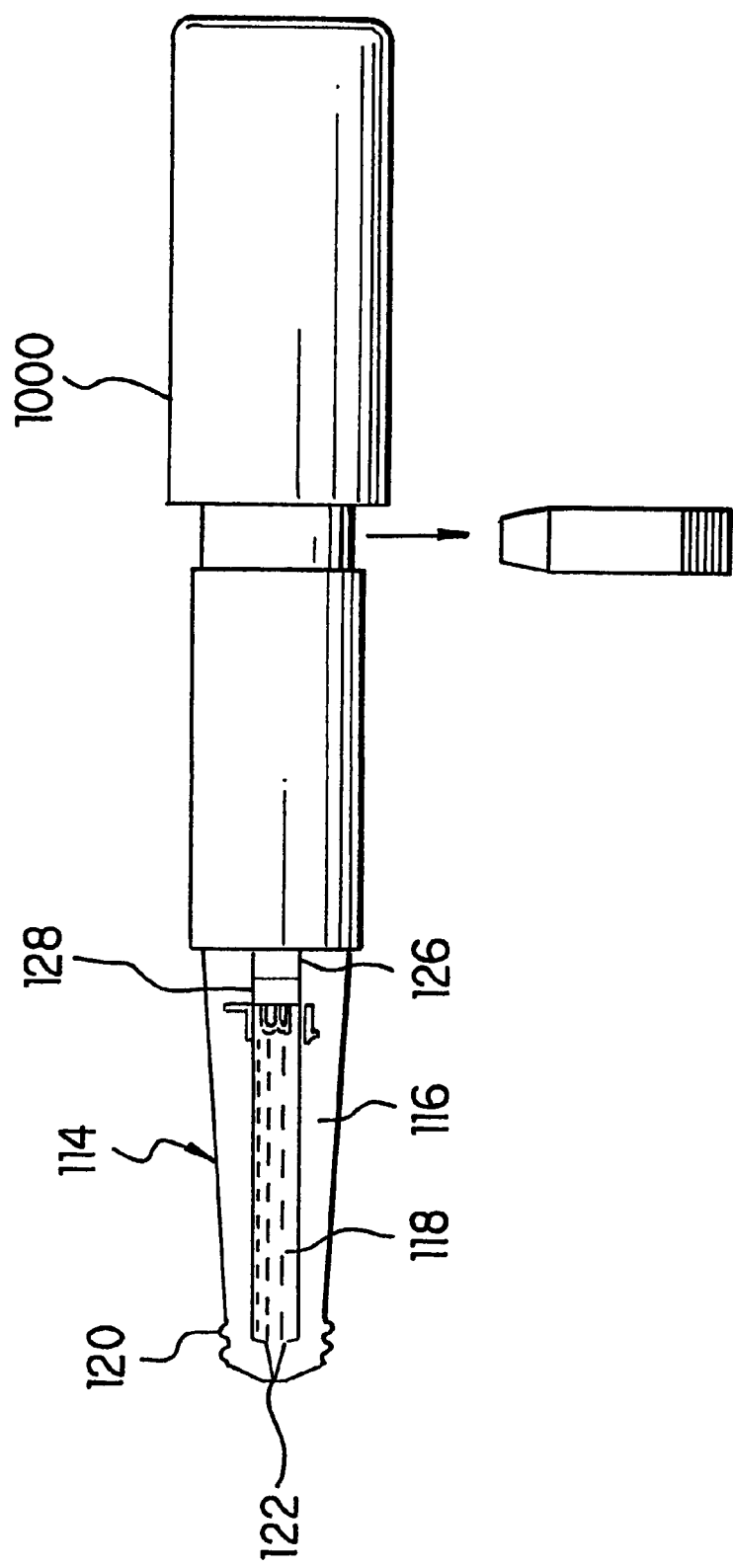
FIG. 18 is a partial cross-sectional and side plan view of the assembled needle-less injector prior to administering an injection in accordance with another embodiment of the present invention.

As shown in FIGS. 12–18, the reagent holder 114 stores the reagent and is configured for sterile docking (or coupling) with the diluent holder 112 containing the diluent. When the diluent holder 112 is docked with the reagent holder 114, the diluent plunger 164 and piston 168 are moved towards the opening 162 in the housing 156 to load the diluent in the reagent holder 114. In preferred embodiments, reagent holder 112 is the ampule for a needle-less injector or the like. As shown in FIG. 16, after loading the reagent holder 114 with diluent, the diluent plunger 164 is withdrawn a distance along the interior chamber 158 to remove any air bubbles, and then the diluent holder 112 is removed and discarded. In alternative embodiments, after loading the reagent holder 114 (that is not connected to a needle-less injector 1000) with diluent, the reagent plunger and the bushing are used to remove any air or bubbles, and then the diluent holder 112 removed and discarded from the reagent holder 114, in a manner and structure similar to that described above in the first embodiment. The reagent holder 114, if an ampule that is separated from a needle-less injector 1000, is then threaded onto the body of a needle-less injector 1000.

In alternative embodiments, if the reagent holder 114 is not an ampule for a needle-less injector, the reagent holder 114, may be removed after receiving the diluent, and then coupled to an ampule for filling with the mixed medication. In further embodiments, the reagent holder 114 may be an ampule for a multi-use needle-less injector, syringe or the like.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A method of mixing medication and filling an ampule of a needle-less injector suitable for injecting liquid medication, the method comprising the steps of:

providing a reagent holder containing a reagent;

providing a diluent holder containing a diluent;

providing the diluent holder with a diluent plunger rod;

coupling the reagent holder to the diluent holder to provide fluid communication between the reagent holder and the diluent holder;

depressing the diluent plunger rod to load the diluent into the reagent holder to mix with the reagent to produce the liquid medication for filling the ampule of the needle-less injector;

providing the reagent holder with a reagent plunger rod; and depressing the reagent plunger rod, after the reagent and the diluent are mixed in the reagent holder to produce the liquid medication, to load the liquid medication into the diluent holder for filling the ampule of the needle-less injector.

2. A method in accordance with claim 1, wherein the diluent holder is formed as the ampule of the needle-less injector.

* * * * *